(12) United States Patent
Crook et al.

(10) Patent No.: US 11,776,684 B2
(45) Date of Patent: Oct. 3, 2023

(54) METHOD AND DEVICE FOR MANAGING ENERGY USAGE BY A MEDICAL DEVICE

(71) Applicant: Pacesetter, Inc, Sylmar, CA (US)

(72) Inventors: Jeffery Crook, Belmont, CA (US); Perry Li, Arcadia, CA (US); Robert J. Williams, San Jose, CA (US)

(73) Assignee: Pacesetter, Inc, Sylmar, CA (US)

( * ) Notice: Subject to any disclaimer, the term of this patent is extended or adjusted under 35 U.S.C. 154(b) by 763 days.

(21) Appl. No.: 16/670,455

(22) Filed: Oct. 31, 2019

(65) Prior Publication Data

US 2021/0098124 A1 Apr. 1, 2021

Related U.S. Application Data

(60) Provisional application No. 62/906,257, filed on Sep. 26, 2019.

(51) Int. Cl.
*G16H 40/63* (2018.01)
*A61N 1/378* (2006.01)
(Continued)

(52) U.S. Cl.
CPC ............ *G16H 40/63* (2018.01); *A61N 1/378* (2013.01); *H02J 3/28* (2013.01); *H02J 3/32* (2013.01); *H02J 7/0013* (2013.01); *H02J 7/0048* (2020.01)

(58) Field of Classification Search
CPC .... A61N 1/378; H02J 3/28; H02J 3/32; H02J 7/0013; H02J 7/0048; H02J 7/342; H02J 7/345
See application file for complete search history.

(56) References Cited

U.S. PATENT DOCUMENTS 5,458,624 A * 10/1995 Renirie ............... A61N 1/378
607/29
5,591,212 A * 1/1997 Keimel ............... A61N 1/378
607/5
(Continued)

FOREIGN PATENT DOCUMENTS

EP 2478935 A2 7/2012
EP 3417908 A1 12/2018

OTHER PUBLICATIONS

International Search Report and Written Opinion for corresponding PCT Application No. PCT/US2020/043880 dated Oct. 26, 2020 (13 pages).

*Primary Examiner* — David V Henze-Gongola
(74) *Attorney, Agent, or Firm* — THE SMALL PATENT LAW GROUP LLC; Dean D. Small

(57) ABSTRACT

A medical device and method are provided. The medical device includes a battery, a charge bank configured to store supplemental energy, memory to store program instructions, and device operational circuitry. The device operational circuitry identifies an energy demand (ED) action to be performed by the device operational circuitry in connection with at least one of monitoring a medical characteristic of interest (COI), treating the medical COI, or wirelessly communicating with a separate device. The device operational circuitry obtains an energy consumption estimate for an amount of energy to be consumed by the device operational circuitry in connection with performing the ED action and dispatches a charge instruction to charge the charge bank from the battery with supplemental energy. The device operational circuitry supplies the supplemental energy to the device operational circuitry for performing the ED action in connection with the at least one of monitoring, treating or communicating operations.

20 Claims, 5 Drawing Sheets

(51) Int. Cl.
*H02J 3/28* (2006.01)
*H02J 3/32* (2006.01)
*H02J 7/00* (2006.01)

(56) References Cited

U.S. PATENT DOCUMENTS

| | | | |
|---|---|---|---|
| 2004/0059392 A1* | 3/2004 | Parramon | A61N 1/375 607/36 |
| 2007/0040449 A1* | 2/2007 | Spurlin | A61M 5/1723 307/64 |
| 2007/0060980 A1 | 3/2007 | Strother et al. | |
| 2011/0106213 A1 | 5/2011 | Davis et al. | |
| 2016/0228708 A1* | 8/2016 | Ternes | A61N 1/36842 |
| 2018/0372805 A1* | 12/2018 | Fischer | G01R 31/3648 |

\* cited by examiner

METHOD AND DEVICE FOR MANAGING ENERGY USAGE BY A MEDICAL DEVICE

CROSS-REFERENCE TO RELATED APPLICATIONS

This application claims priority to U.S. Provisional Application Ser. No. 62/906,257, filed on Sep. 26, 2019, the entire disclosure of which is incorporated herein by reference.

BACKGROUND

Embodiments of the present disclosure generally relate to methods and devices for managing energy usage by a medical device.

Today, the Bluetooth low energy (BLE) protocol has become a prevalent method for communication between implantable medical devices and external devices (or other implanted medical devices). Various battery technologies are used in implantable devices in order to offer highly compact physical shapes with high energy densities. However, compact, high energy batteries exhibit certain limits, such as a large equivalent series resistance (ESR) as compared to prior battery designs that are less compact and/or have lower energy density. Batteries that exhibit a large ESR experience an unduly large temporary drop in battery voltage when certain high current demands are placed on the battery. A BLE communication is one example of an operation performed by an implantable device that causes large ESR batteries to experience an unduly large temporary voltage drop. In some instances, the voltage drop may be sufficient to cause the implantable device to initiate a reset operation. Among other things, when the implantable device undergoes a reset operation, the device drops the communications session. The foregoing concern with dropped communications is particularly of interest for implantable devices that are extremely small and located at deep locations within the patient's body, such as leadless pacemakers and other leadless devices implanted within the heart. Leadless pacemakers use very small batteries yet have high current demands.

Heretofore, attempts to address the foregoing concern have included: 1) permanently fixing additional large capacitors onto the primary source, 2) selecting a less compact battery chemistry or 3) leaving unused battery capacity within the battery to maintain higher, usable voltage levels. These alternate approaches have negative impacts that reduce longevity, product performance and physical shape/size.

A need remains for methods and devices that overcome the foregoing and other disadvantages of conventional approaches.

SUMMARY

In accordance with embodiments herein, a medical device is provided. The medical device includes a battery, a charge bank configured to store supplemental energy, memory to store program instructions, and device operational circuitry. The device operational circuitry includes at least one of a transceiver, circuitry or processor configured to execute the program instructions. The device operational circuitry identifies an energy demand (ED) action to be performed by the device operational circuitry in connection with at least one of monitoring a medical characteristic of interest (COI), treating the medical COI, or wirelessly communicating with a separate device. The device operational circuitry obtains an energy consumption estimate for an amount of energy to be consumed by the device operational circuitry in connection with performing the ED action. The device operational circuitry dispatches, based on the energy consumption estimate, a charge instruction to charge the charge bank from the battery with supplemental energy. The device operational circuitry supplies the supplemental energy, from the charge bank, to the device operational circuitry for performing the ED action in connection with the at least one of monitoring, treating or communicating operations.

Optionally, the device operational circuitry may be further configured to toggle the charge bank in and out of a power supply loop formed between the battery and at least one of the transceiver, circuitry or processor. The toggling operation may be based on when the energy consumption estimate exceeds an energy threshold. The device operational circuitry may be configured to add the supplemental power from the charge bank when the battery cannot supply the energy consumption estimate without experiencing a battery voltage dip below a battery voltage threshold. The charge instruction may be configured to perform a background charging operation to selectively interconnect the charge bank to the battery prior to a scheduled time before the ED action. The background charging operation may siphon energy from the battery at a predetermined background charge rate that avoids the battery from experiencing a battery voltage dip below a battery voltage threshold. The ED action may include initiating a wireless communications session. The device operational circuitry may include a dispatcher configured to dynamically adjust a transmission parameter utilized in connection with the wireless communications session. The transmission parameter that is updated may include adjusting at least one of transmit packet size, transmit packet number, packet transmission rate, or signal power. The battery may exhibit a primary source limit. The charge bank may supply the supplemental power when the energy consumption estimate exceeds the primary source limit. The device operational circuitry may be further configured to implement first or second charge operations based on a type of the ED action. The charge bank may comprise multiple capacitors, from which a subset of the multiple capacitors may be activated based on an amount of the supplemental energy associated with the type of the ED action. The energy consumption estimate may estimate the power demand associated with performing the communicating operation contemporaneous in time with at least one of the monitoring or treating operations. The device operational circuitry may further comprise a dispatcher configured to at least one of skip, delay or modify the at least one of monitoring or treating operation when the energy consumption estimate exceeds a primary source limit of the battery. The medical device may represent at least one of an implantable medical device, a diabetes monitoring device, a body generated analyte (BGA) test device, and a pulmonary arterial pressure monitor.

In accordance with embodiments herein, a method for managing energy usage of a medical device is provided. The method identifies an energy demand (ED) action to be performed by device operational circuitry of the medical device in connection with at least one of monitoring a medical characteristic of interest (COI), treating the medical COI, or wirelessly communicating with a separate device. The device operational circuitry includes at least one of a transceiver, circuitry or processor. The method obtains an energy consumption estimate for an amount of energy to be consumed by the device operational circuitry in connection with performing the ED action. The method dispatches, based on the energy consumption estimate, a charge instruction to charge a charge bank from a battery with supplemental energy. The method supplies the supplemental energy, from the charge bank, to the device operational circuitry for performing the ED action in connection with the at least one of monitoring, treating or communicating operations.

Optionally, the supplying operation includes toggling the charge bank in and out of a power supply loop formed between the battery and at least one of the transceiver, circuitry or processor. The toggling operation may be based on when the energy consumption estimate exceeds an energy threshold. The supplying operation may add the supplemental power from the charge bank when the battery cannot supply the energy consumption estimate without experiencing a battery voltage dip below a battery voltage threshold. The method may perform a background charging operation to selectively interconnect the charge bank to the battery prior to a scheduled time before the ED action. The background charging operation may siphon energy from the battery at a predetermined background charge rate that avoids the battery from experiencing a battery voltage dip below a battery voltage threshold. The ED action may include initiating a wireless communications session. The method may dynamically adjust a transmission parameter utilized in connection with the wireless communications session. The transmission parameter that is updated may include adjusting at least one of transmit packet size, transmit packet number, packet transmission rate, or signal power. The battery may exhibit a primary source limit. The charge bank may supply the supplemental power when the energy consumption estimate exceeds the primary source limit. The obtaining the energy consumption estimate may estimate the power demand associated with performing the communicating operation contemporaneous in time with at least one of the monitoring or treating operations. The method may include at least one of skipping, delaying or modifying the at least one of monitoring or treating operation when the energy consumption estimate exceeds a primary source limit of the battery. The method may implement one of first or second charge operations based on a type of the ED action. The first and second charge operations may have different first and second supplemental energies, respectively. The charge bank may include multiple capacitors. The method may activate a subset of the multiple capacitors based on an amount of the supplemental energy associated with a type of the ED action. The method may verify a battery state and dynamically adjust a parameter in connection with at least one of the monitoring, treating or communicating operations based on the battery state.

BRIEF DESCRIPTION OF THE DRAM/TNGS

Figure 4:
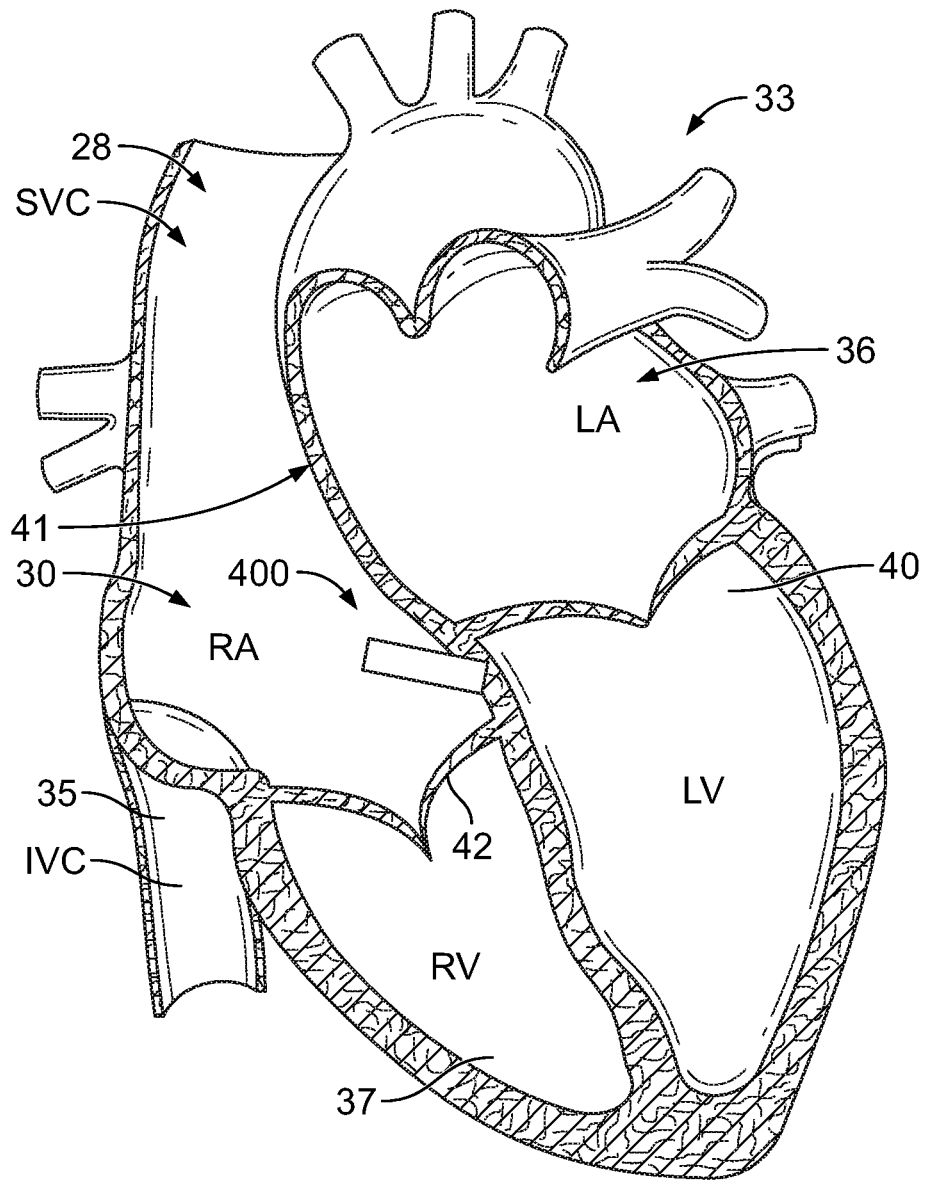

FIG. 4 provides a sectional view of a patient's heart and shows a leadless intra-cardiac medical device in accordance with embodiments herein.

Figure 5A:
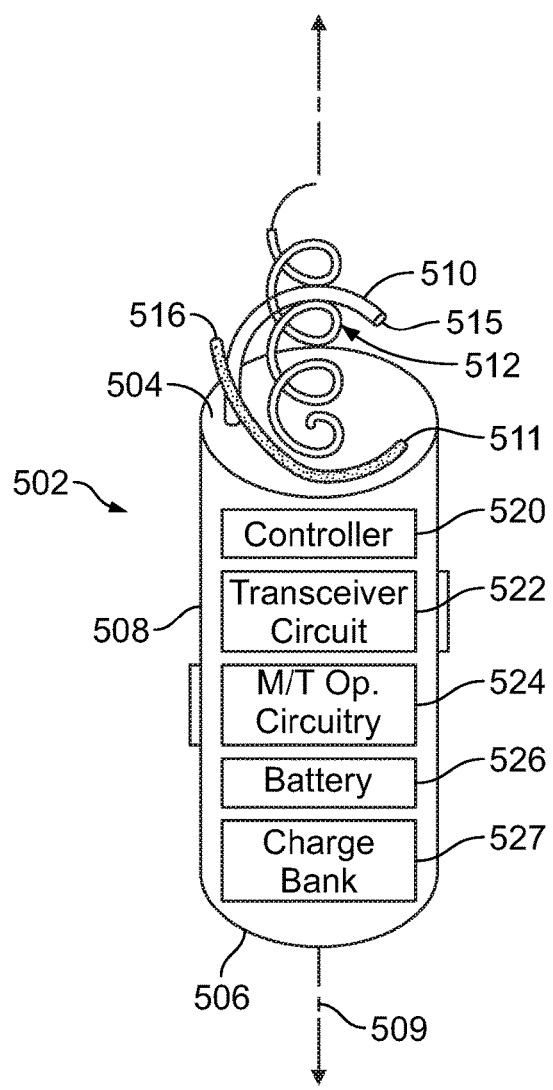

FIG. 5A illustrates a side perspective view of the LIMD of FIG. 4 oriented with the base facing upward to illustrate electrodes in more detail in accordance with embodiments herein.

Figure 5B:
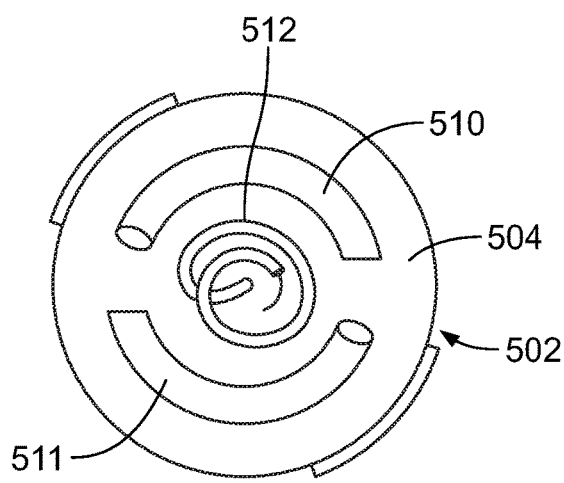

FIG. 5B illustrates a bottom plan view of the LIMD in accordance with embodiments herein.

Figure 6:
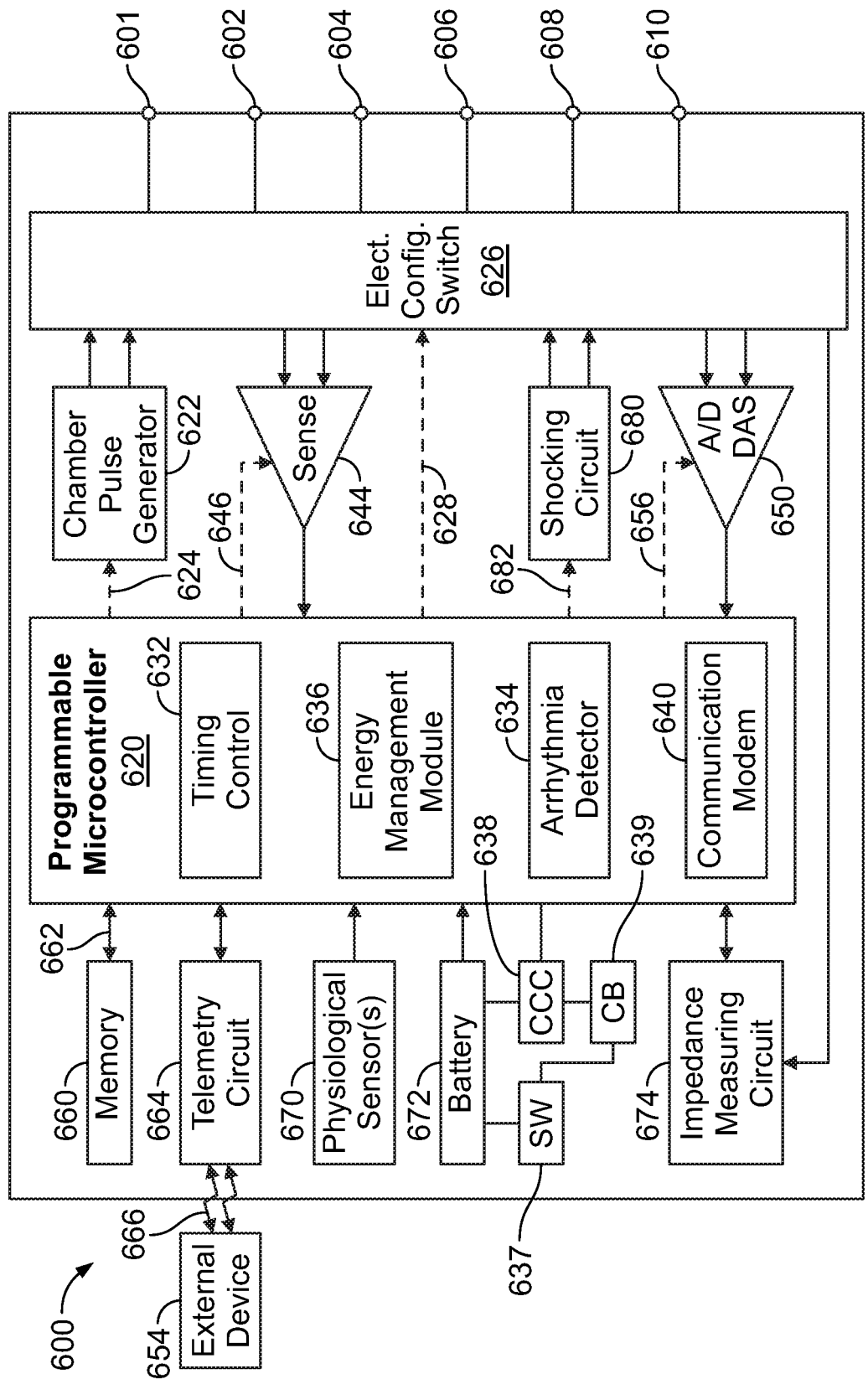

FIG. 6 shows an exemplary LIMD configured for dual-chamber functionality from a primary location within a single chamber of the heart in accordance with embodiments herein.

DETAILED DESCRIPTION

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. Further, the methods may be fully or partially implemented by one or more processors of one or more devices or systems. While the operations of some methods may be described as performed by the processor(s) of one device, additionally, some or all of such operations may be performed by the processor(s) of another device described herein.

All references, including publications, patent applications and patents, cited herein are hereby incorporated by reference to the same extent as if each reference were individually and specifically indicated to be incorporated by reference and were set forth in its entirety herein.

The term "hermetic", as used herein, shall refer to a sealed interface at least with respect to entry or escape of air and/or bodily fluids.

The term "IMD data" shall refer to any and all types of information and signals conveyed from an implantable medical device to a local or remote external device. Non-limiting examples of IMD data include cardiac activity signals (e.g., intracardiac electrogram or IEGM signals), impedance signals (e.g., cardiac, pulmonary or transthoracic impedances), accelerometer signatures (e.g., activity signals, posture/orientation signals, heart sounds), pulmonary arterial pressure signals, MCS rpm levels, MCS flow rates, device alerts and the like.

The terms "body generated analyte" and "BGA" shall mean a test substance or specimen that is naturally generated by or naturally present in a human body. The test substance or specimen may be in liquid form (e.g., blood or other bodily fluid), solid form (e.g., tissue, fat, muscle, bone, or other organ-based material), gas form, cellular form or otherwise. Non-limiting examples of body generated analytes include hematocrit, troponin, CKMB, BNP, beta human chorionic gonadotropin (bHCG), carbon dioxide partial pressure ($pCO_2$), partial pressure oxygen ($pO_2$), pH, PT, ACT, activated partial thromboplastin time (APTT), sodium, potassium, chloride, calcium, urea, glucose, creatinine, lactate, oxygen, and carbon dioxide, thyroid stimulating hormone, parathyroid hormone, D-dimer, prostate specific antibody, $TCO_2$, Anion Gap, ionized calcium, urea nitrogen, lactose, hemoglobin, pH, $PCO_2$, $PO_2$, $HCO_3$, Base Excess, $O_2$, ACT Kaolin, ACT Celite, PT/INR, β-hCG, cTnI, CK-MB, BNP and the like, and combinations thereof. The analyte may be tested in a liquid sample that is whole blood, however other samples can be used including blood, serum, plasma, urine, cerebrospinal fluid, saliva and amended forms thereof. Amendments can include diluents and reagents such as anticoagulants and the like.

The term "BGA test device" shall mean any and all equipment, devices, disposable products utilized to collect and analyze a BGA.

The term "BGA data" shall refer to any and all types of information and signals conveyed from a BGA test device to a local or remote device. Nonlimiting examples of BGA data include glucose level levels, glucose trends, levels/trends for any other type of body generated analyte and the like.

The term "patient data" shall comprise both IMD data and BGA data.

The term "ESR" shall mean equivalent series resistance. A battery may be modeled as a voltage source in series with a resistance. In practice, the internal resistance of a battery is dependent on its size, chemical properties, age, temperature, and the discharge current. It has an electronic component due to the resistivity of the component materials and an ionic component due to electrochemical factors such as electrolyte conductivity, ion mobility, and electrode surface area. Measurement of the internal resistance of a battery is a guide to its condition but may not apply at other than the test conditions. The internal resistance of a battery $R_{int}$ may be calculated from its open circuit voltage $V_{NL}$, load voltage $V_{FL}$, and the load resistance $R_L$: $=[V_{NL}/V_{FL}-1]*R_L$. The equivalent series resistance can be used to estimate battery internal resistance, particularly to check the state of discharge of a battery.

The terms "energy demand action" and "ED action" refer to one or more operations performed by the electronic circuitry within a medical device, where the electronic circuitry, when performing the operation or operations, will use an amount of power that is sufficiently high to potentially cause a temporary battery voltage drop given a current power state of the battery. For example, in connection with a communications operation, the ED action may represent one or more of a) transmission of an advertisement, b) transmission of one or more data packets, and c) a schedule or cycle length between transmission of successive data packets. As another example, in connection with monitoring a medical COI, the ED action may represent one or more of a) sensing cardiac activity, b) converting analog cardiac activity signals to digital cardiac activity signals, c) analyzing a medical COI from the digital CA signals and d) recording the medical COI. Other examples of monitoring operations include sensing heart sounds, patient activity, patient posture/orientation and the like. As another example, in connection with treating the medical COI, the ED action may represent one or more of a) identifying a treatment for the medical COI, b) delivering the treatment, and c) recording the treatment. Various pacing and other low voltage treatments utilize different amounts of energy (e.g., different pacing voltages, pulse widths, duty cycles, antitachycardia pacing (ATP) therapy versus non-ATP therapy).

The phrase "energy consumption" shall mean an amount of energy utilized to power device operational circuitry when performing an ED action. The energy consumption includes two primary types of energy, namely 1) energy consumed by internal device operational circuitry of the medical device (non-pacing energy consumption) and 2) pacing energy delivered as pacing pulses. For the avoidance of doubt, the phrases "energy consumption" and "amount of energy" do not include and do not refer to energy delivered to a patient during medium voltage or high-voltage shocks (e.g., cardioversion shocks, defibrillation shocks, etc.). Non-limiting examples of non-pacing energy consumption by internal device operational circuitry include when a transceiver utilizes a predetermined first amount of energy in connection with transmitting an RF advertisement (BLE), predetermined second amount of energy in connection with transmitting a known amount of data during a BLE communications session. Other examples of amounts of non-pacing energy consumption by internal device operational circuitry include the energy consumed by sensing circuitry within a medical device when monitor a medical COI, such as to monitor cardiac activity signals, heart sounds, activity data, impedance data, body generated analytes (e.g., glucose) and the like. As an example of pacing energy consumption, when delivering a pacing therapy, pacing circuitry may utilize a predetermined amount of pacing energy that is delivered through one or more pacing pulses.

Embodiments herein monitor energy demand (ED) events (e.g., BLE usage) and estimate/predict future ED action usage algorithmically while coordinating future ED actions to be synchronized with a designated charge bank to render sufficient energy available and avoid an undue dip in battery voltage during ED actions. Additionally or alternatively, embodiments dynamically change parameters associated with the ED action to adjust the energy demand associated with the ED action. For example, when the ED action corresponds to a communications session, embodiments may adjust a size and/or number of transmitted packets, a period of time between packet transmissions, and/or transmit signal power. The parameters associated with the ED action may be adjusted to maintain the resultant energy demand of the ED action within a capacity of the battery and charge bank, and/or when the application or environment warrants more efficient use of communication.

In accordance with aspects herein, embodiments enable robust BLE communication on highly miniaturized devices, such as a leadless pacemaker while maintaining standard of care device longevity. In accordance with aspects herein, embodiments increase product longevity with BLE usage through a given battery end-of-service period (e.g., not leaving any battery capacity unused within the battery). In accordance with aspects herein, embodiments allow smaller and more compact battery chemistry selection for a given design (yielding smaller products). As battery chemistry becomes more compact, the battery typically exhibits a higher ESR.

In accordance with aspects herein, embodiments provide improved management of BLE communications. The ability to dynamically change BLE transmission parameters (or other event related parameters) to work in coordination with the charging bank ensures robustness of BLE communication (or other operations). In accordance with aspects herein, embodiments improve transmission power through a given battery end-of-service period, therefore affording improved product performance through full lifecycle and improved product consistency.

In accordance with aspects herein, embodiments improve depth of implants through additional power availability for a given battery ESR. In accordance with aspects herein, embodiments improve efficiency as compared with prior designs that have large banks of capacitors permanently connected to the primary source. If a capacitor bank is permanently connected to the battery, the system will experience leakage that will draw down the battery constantly.

Embodiments may be implemented in connection with one or more medical devices, including both portable external medical devices and/or implantable medical devices (IMDs). By way of example, embodiments may be implemented in connection with one or more of the methods, devices and systems described in U.S. Provisional Application Ser. No. 62/875,870, titled "Methods, Devices and Systems for Holistic Integrated Healthcare Patient Management", filed Jul. 18, 2019, which is hereby incorporated by reference in its entirety. Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method and System to Treat Apnea" and U.S. Pat. No. 9,044,610 "System and Methods for Providing a Distributed Virtual Stimulation Cathode for Use with an Implantable Neurostimulation System", which are hereby incorporated by reference.

Additionally or alternatively, the IMD may include one or more structural and/or functional aspects of the device(s) described in U.S. Pat. No. 9,216,285 "Leadless Implantable Medical Device having Removable and Fixed Components" and U.S. Pat. No. 8,831,747 "Leadless Neurostimulation Device and Method Including the Same", which are hereby incorporated by reference. Additionally or alternatively, the IMD may include one or more structural and/or functional aspects of the device(s) described in U.S. Pat. No. 8,391,980 "Method and System for Identifying a Potential Lead Failure in an Implantable Medical Device" and U.S. Pat. No. 9,232,485 "System and Method for Selectively Communicating with an Implantable Medical Device", which are hereby incorporated by reference.

Additionally or alternatively, the IMD may be a subcutaneous IMD that includes one or more structural and/or functional aspects of the device(s) described in U.S. application Ser. No. 15/973,195, titled "Subcutaneous Implantation Medical Device with Multiple Parasternal-Anterior Electrodes" and filed May 7, 2018; U.S. application Ser. No. 15/973,219, titled "Implantable Medical Systems and Methods Including Pulse Generators and Leads" filed May 7, 2018; US Application Ser. No.: 15,973, 249, titled "Single Site Implantation Methods for Medical Devices Having Multiple Leads", filed May 7, 2018, which are hereby incorporated by reference in their entireties. Further, one or more combinations of IMDs may be utilized from the above incorporated patents and applications in accordance with embodiments herein.

Additionally or alternatively, the IMD may be a leadless cardiac monitor (ICM) that includes one or more structural and/or functional aspects of the device(s) described in U.S. patent application Ser. No., 9,949,660, issued Apr. 24, 2018, U.S. patent application Ser. No., 15,084,373, filed Mar. 29, 2016, entitled, "Method and System to Discriminate Rhythm Patterns in Cardiac Activity," which is expressly incorporated herein by reference.

Additionally or alternatively, the medical device may represent a BGA test device. The BGA test device may implement one or more of the methods, devices and systems described in the following publications, all of which are incorporated herein by reference in their entireties: U.S. Pat. No. 8,514,086, entitled "Displays for a Medical Device", issued Aug. 20, 2013; U.S. Patent Publication Number 2011/0256024, entitled "Modular Analyte Monitoring Device", published Oct. 20, 2011; U.S. Patent Publication Number 2010/0198142, entitled "Multifunction Analyte Test Device and Methods Therefore", published Aug. 5, 2010; U.S. Patent Publication Number 2011/0160544, entitled "System and Method for Analysis of Medical Data to Encourage Healthcare Management", published Jun. 30, 2011; U.S. Pat. No. 5,294,404, entitled "Reagent Pack for Immunoassays" issued Mar. 15, 1994; U.S. Pat. No. 5,063,081, entitled "Method of Manufacturing a Plurality of Uniform Microfabricated Sensing Devices Having an Immobilized Ligand Receptor" issued Nov. 5, 1991; U.S. Pat. No. 7,419,821, entitled "Apparatus and Methods for Analyte Measurement and Immunoassay" issued Sep. 2, 2008; U.S. Patent Publication Number 2004/0018577, entitled "Multiple Hybrid Immunoassays" published Jan. 29, 2004; U.S. Pat. No. 7,682,833, entitled "Immunoassay Device with Improved Sample Closure" issued Mar. 23, 2010; U.S. Pat. No. 7,723,099, entitled "Immunoassay Device with Immuno-Reference Electrode" issued May 25, 2010; and Baj-Rossi et al. "Fabrication and Packaging of a Fully Implantable Biosensor Array", (2013) IEEE, pages 166-169; U.S. Patent Publication Number 2011/0160544, entitled "System and Method for Analysis of Medical Data to Encourage Healthcare Management", published Jun. 30, 2011; U.S. Patent Publication Number 2019/0151541, entitled "Integrated Analyte Sensor and Infusion Device and Methods Therefor", published May 23, 2019; U.S. Patent Publication Number 2010/0100580, entitled "Blood Glucose Tracking Apparatus and Methods", published Apr. 22, 2010; U.S. Patent Publication Number 2010/0098583, entitled "Blood Glucose Tracking Apparatus and Methods", published Apr. 22, 2010; U.S. Patent Publication Number 2019/0167165, entitled "Analyte Monitoring Device and Methods of Use", published Jun. 6, 2019; U.S. Patent Publication Number 2019/0159734, entitled "Method and System for Providing Analyte Monitoring", published May 30, 2019; U.S. Patent Publication Number 2019/0159706, entitled "Method and Apparatus for Providing Dynamic Multi-Stage Signal Amplification in a Medical Device", published May 30, 2019; U.S. Patent Publication Number 2019/0216374, entitled "Analyte Sensors with a Sensing Surface Having Small Sensing Spots", published Jul. 18, 2019; U.S. Patent Publication Number 2019/0209059, entitled "Analyte Monitoring Device and Methods of Use", published Jul. 11, 2019; U.S. Patent Publication Number 2019/0192071, entitled "Method And Apparatus For Determining Medication Dose Information", published Jun. 27, 2019; U.S. Patent Publication Number 2009/0055149, entitled "Method And System For Determining Analyte Levels", published Feb. 26, 2009; U.S. Patent Publication Number 2009/0054750, entitled "Method And System For Providing Integrated Analyte Monitoring And Infusion System Therapy Management" published Feb. 26, 2009; U.S. Patent Publication Number 2009/0054745, entitled "Method And System For Providing Data Management In Integrated Analyte Monitoring And Infusion System", published Feb. 26, 2009; U.S. Patent Publication Number 2008/0319294, entitled "Health Management Devices And Methods", published Dec. 25, 2008; U.S. Patent Publication Number 2008/0269672, entitled "Analyte Monitoring Device And Methods Of Use", published Oct. 30, 2008; U.S. Patent Publication Number 2008/0021291, entitled "Integrated Lancet And Blood Glucose Meter System", published Jan. 24, 2008; U.S. Patent Publication Number 2007/0244380, entitled "Analyte Monitoring Device And Methods Of Use", published Oct. 18, 2007; U.S. Patent Publication Number 2010/0069732, entitled "Medical Devices And Methods Of Using The Same", published Mar. 18, 2010; U.S. Patent Publication Number 2010/0068796, entitled "Blood Glucose Tracking Apparatus And Methods", published Mar. 18, 2010; U.S. Patent Publication Number 2010/0066542, entitled "Health Management Apparatus And Methods", published Mar. 18, 2010; and U.S. Patent Publication Number 2010/0049131, entitled "Device And Method Employing Shape Memory Alloy", published Feb. 25, 2010; and U.S. Patent Publication Number 2014/0221771, entitled "Method And Implantable System For Blood-Glucose Concentration Monitoring Using Parallel Methodologies" published Aug. 7, 2014.

Embodiments herein may be implanted in connection with point-of-care or POC methods, devices and systems described in one or more of the following publications, all of which are expressly incorporated herein by reference in their entireties: U.S. Pat. No. 6,786,874, entitled "Apparatus And Method For The Collection Of Interstitial Fluids" issued Sep. 7, 2004; U.S. Pat. No. 9,494,578, entitled "Spatial Orientation Determination In Portable Clinical Analysis Systems" issued Nov. 15, 2016; and U.S. Pat. No. 9,872,641, entitled "Methods, Devices And Systems Related To Analyte Monitoring" issued Jan. 23, 2018.

In accordance with embodiments herein, a dispatcher is configured to track energy usage, manage scheduled ED actions, monitor a battery state, adjust parameters associated with one or more communications, monitoring or treatment operations, and manage a background charging operation of the charge bank. The types of parameters that are adjusted may vary based on the operation. As nonlimiting examples, in connection with a communications operation, the dispatcher may adjust data packet size, a schedule at which data packets are transmitted, signal strength and the like. As a further nonlimiting example, in connection with a monitoring operation, the dispatcher may adjust electrode configurations used to define sensing channels, the number and/or direction of sensing channels, a power level utilized to collect signals indicative of the COI. As a further example, during a monitoring operation, the dispatcher may determine whether to collect intracardiac electrogram (IEGM) signals, impedance signals, heart sound signals, accelerometer signals indicative of heart sounds and/or activity, BGA data and the like. During a monitoring operation, the dispatcher may change a time period between sensing operations, an amount of data collected in connection with individual arrhythmias, a number of beats for which cardiac activity data is combined (e.g., to form ensembles) and the like. In connection with a therapy operation, the dispatcher may determine whether to deliver certain types of pacing therapy, adjust electrode configurations used to deliver therapy, a number of pacing pulses delivered, a pacing pulse amplitude, pacing pulse width, pacing pulse duty cycle and the like.

Figure 1:
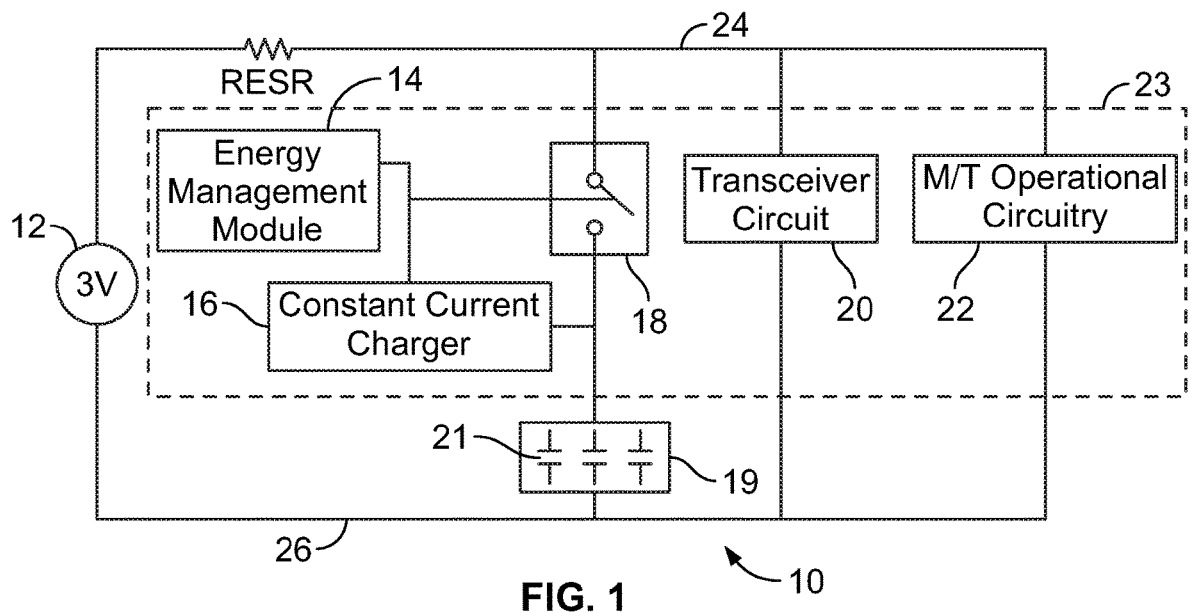
FIG. 1 illustrates a block diagram of a portion of a medical device implemented in accordance with embodiments herein.

FIG. 1 illustrates a block diagram of a portion of a medical device implemented in accordance with embodiments herein. It should be recognized that not all of the components within the medical device are illustrated in FIG. 1. The device 10 is generally shown to include a battery 12 that is connected, through power supply lines 24, 26, to various device operational circuitry (as noted by dashed line 23). By way of example, the device operational circuitry 23 includes an energy management module 14, a constant current charger 16, a switch 18, a charge bank 19, a transceiver circuit 20 and monitoring and/or therapy (M/T) operational circuitry 22. While illustrated as separate blocks, it is recognized that the energy management module 14, constant current charger 16, switch 18 and transceiver circuit 20 represent a portion of the M/T operational circuitry 22. While not shown, it is recognized that the electronic circuitry generally includes, among other things, various sensing circuitry, amplifiers, energy storage components, firmware, hardware, processors, memory, and the like. Further examples of the electronic circuitry are described below and illustrated in further block diagrams of embodiments herein.

The M/T operational circuitry 22 generally refers to, among other things, various sensing circuitry, amplifiers, energy storage components, firmware, hardware, processors, memory, and the like, that are utilized to perform various actions in connection with the overall operation of the medical device 10. For example, the M/T operational circuitry 22 may include sensing circuitry, analog/digital converters, firmware, processors and memory that are configured to perform all or a portion of the actions associated with monitoring a medical characteristic of interest (COI). As another example, the device operational circuitry may include charge storage components, firmware, processors and memory that are configured to perform all or a portion of the actions associated with treating the medical COI. The transceiver circuit 20, alone or in combination with the M/T operational circuitry 22, performs all or a portion of the actions associated with wirelessly communicating with a separate device, such as a local external device, an implanted device and the like. As one nonlimiting example, the M/T operational circuitry 22 may include sensing circuitry to monitor heart sounds, where the heart sound monitoring circuitry may consume a relatively large amount of energy while sensing heart sounds.

The energy management module 14 performs various operations as described herein, such as scheduling ED actions, obtaining energy demands to perform the ED actions, dispatching charge instructions to charge the charge bank 19 and managing supply of supplemental energy from the charge bank 19 to the device operational circuitry 23. The energy management module 14 controls the constant current charger 16 during a charging operation to charge the charge bank 19 from the battery 12 with supplemental energy. During a subsequent ED action, the energy management module 14 directs the switch 18 to selectively interconnect the charge bank 19 between the power supply lines 24, 26 to add the charge bank 19 as a secondary energy source in addition to the battery 12 which represents the primary energy source. The energy management module 14 toggles charge bank 19 into and out of the power supply loop, when necessary to provide an additional energy source as intermittently required for scheduled high energy demand actions. The battery 12 exhibits a primary source limit, while the charge bank 19 supplies the supplemental power when the energy consumption estimate exceeds the primary source limit of the battery.

The additional energy source (the charge bank 19) is charged through a syphon from the battery 12 when the battery 12 is at a state in which the battery 12 cannot otherwise separately and individually supply the energy demanded by the heavy energy demand action. Energy is syphoned over time from the battery 12 to the charge bank 19 at a predetermined background rate for a background period of time prior to initiating the ED action. By selectively and intermittently connecting and disconnecting the charge bank 19 to the battery 12, the energy management module 14 allows for added circuit efficiency by avoiding a permanent connection/load between the battery 12 and the charge bank 19. The charge bank 19 includes one or more charge storage devices 21 (e.g., one or more capacitors or other devices). In general, a bank of capacitors may exhibit a certain amount of energy leakage over time. When a capacitor is permanently connected to a battery that seeks to maintain the capacitor in a fully charged state at all times, the capacitor places an undo continuous load on the battery that would otherwise slowly drain the battery. The energy management module 14 avoids a permanent connection between the battery 12 and charge bank 19 to avoid such an undue permanent load on the battery 12 and thereby avoids slowly draining on the battery 12 due to capacitor energy leakage.

The energy management module 14 implements a dispatcher that implements an iterative feedback loop to support adequate operation of ED actions (e.g., BLE communications) while transferring energy to the charge bank 19 at a slower background rate over non-ED intervals during which the electronic circuitry does not perform an ED action. The energy management module 14 balances transmission usage and other ED actions that require increased current draw to avoid problematic temporary battery voltage dips, thereby preventing system resets among other problems. By utilizing a feedback loop, the energy management module 14 monitors a condition of the battery 12 throughout the battery life. In high ESR batteries or towards the end-of-service in other batteries, the ESR is high and may render the device more susceptible to voltage dip induced resets. The energy management module 14 avoids the problems exhibited by high ESR batteries and other batteries at end-of-life.

While one example embodiment is described in connection with ED actions of radio frequency wireless communications, it is recognized that other types of operations performed by a medical device also utilize unduly high energy demand for short periods of time. The energy management module 14 is configured to account for and manage numerous different types of ED actions, including preparing for multiple ED actions that may be implemented simultaneously and/or in a relatively short successive period of time. The energy management module 14 provides a framework that allows for optimization for a given system through a dispatcher that accounts for other system-specific events. For example, the dispatcher may limit the number of types of ED actions that can be charged/prepared for if another ED action is occurring (e.g., active sampling, other telemetry sessions or full duty cycle processor usage—all of which would place additional 'normal' concurrent strain on the battery). The dispatcher implements dynamic feedback, including automatically updating certain types of ED actions to curb energy usage. For example, the dispatcher may automatically update certain parameters used in connection with an ED action. For example, in connection with a communications operation, the dispatcher may adjust one or more transmission parameters, such as transmission packet lengths. Further, the dispatcher may adjust additional preparation mechanisms and changing the scheduling criteria (allowing for a longer duration of battery recovery time). Battery chemistry typically has a history that slowly recovers from heavy usage. The dispatcher accounts for the battery chemistry as general guidance.

Figure 2:
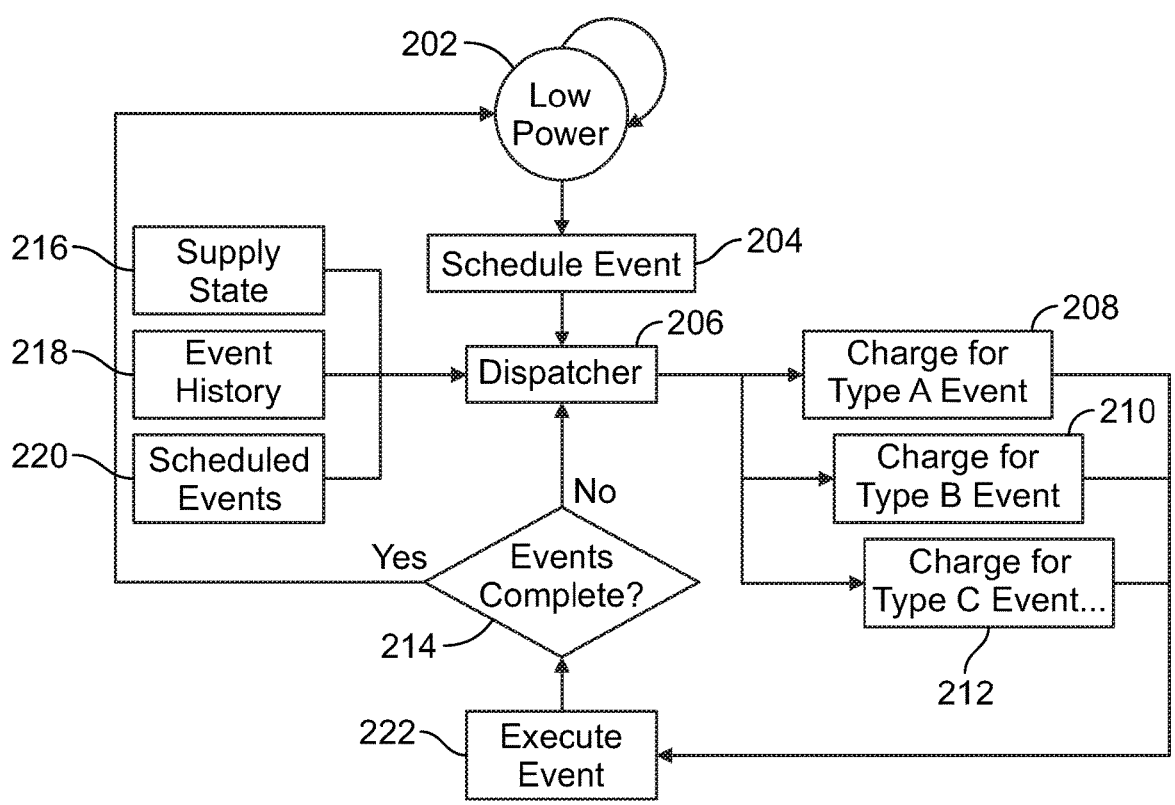
FIG. 2 illustrates a process for managing energy usage of a medical device implemented in accordance with embodiments herein.

FIG. 2 illustrates a process for managing energy usage of a medical device implemented in accordance with embodiments herein. While the following example is described in connection with implementation within a single medical device, it is understood that at least a portion of the operations may be divided between multiple devices. For example, certain operations may be implemented by the medical device, while other operations may be implemented by a local external device and/or remote server. When the operations are split between a medical device and a local external device and/or remote server, information may be conveyed in real time between the various devices. Additionally or alternatively, when the operations are split between a medical device and a local external device and/or remote server, the operations by the local external device and/or remote server may be performed at a separate point in time than (e.g., before) the operations by the medical device. The operations may be implemented by one or more processors, when executing program instructions stored in memory, by one or more controllers implementing firmware, by dedicated hardware circuits, and/or any combination thereof.

At 202, the medical device is maintained in a low-power quiescent state. While in the low-power quiescent state, the device operational circuitry draws relatively little power (or no power). Periodically, the medical device wakes up to perform various operation (e.g., transmit an advertisement pulse, implement a scheduled data transmission to upload data to a local separate device). At 204, the process identifies a scheduled action.

At 206, a dispatcher identifies the type of scheduled action. The dispatcher may be implemented as a hardware circuits, firmware, one or more processors executing programmable instructions, and various combinations thereof. Various types of scheduled actions may occur. The scheduled action may not include an ED action, but instead may concern actions that do not consume sufficient power to be of a concern for potentially lowering the battery voltage. However, other scheduled action may include one or more ED actions to be performed by the device operational circuitry. When the scheduled action includes one or more ED actions, the dispatcher determines at 206 the type of scheduled action and the type of ED action. Various examples of ED actions and scheduled actions are described herein. The process moves from the dispatcher at 206 to one of multiple types of charging operations at 208-212.

At 206, the dispatcher selects the type of charging operation based on the type of scheduled action and/or based on the ED action. Different types of scheduled actions and ED actions have different corresponding energy consumption estimates. The dispatcher obtains the energy consumption estimate associated with the ED action and based thereon flow branches to one of multiple charge operations 208-212. For example, the charge operations at 208-212 may correspond to first, second and third types (A-C) of ED actions, each of which has a corresponding different energy consumption estimate. While the energy consumption is referred to as an "estimate", the energy consumption may be a preprogrammed value, a value measured from a prior similar ED action or otherwise. By way of example, memory may maintain a look up table that includes energy consumption estimates associated with different ED actions. The energy consumption estimates in the look up table may be preprogrammed prior to implant, updated periodically through communication with a local external device and/or automatically calculated by the medical device (or a remote server) during operation. As another example, an algorithm may be implemented within the medical device that calculates an energy consumption estimate based on the ED action.

For example, the type A ED action may correspond to an energy consumption estimate associated with transmitting BLE advertising packets, while the type B ED action may correspond to an energy consumption estimate associated with transmitting one or more data packets during a BLE communications session. The type C ED action may correspond to another action during a communication session and/or an action during a monitoring or treatment operation. As another example, the type of ED action may correspond to a standard alert to be transmitted from the medical device to a separate local device (e.g., a smart phone) such as to inform the smart phone user regarding the current battery state, a low battery condition or a condition or state of another electronic component in the medical device. In general, some standard alerts may utilize very few bytes of data to transmit and thus represent a low demand transmission payload. As another example, the ED action may include a scheduled nightly communications session with a local external device (e.g., a bedside monitor), in which a larger amount of data will be uploaded from the medical device to the local external device and/or a larger amount of data will be downloaded from the local external device to the medical device (e.g., a software or firmware update, adjustment in monitoring and/or therapy parameters). An ED action associated with the standard alert may call for one type of charge operation (e.g., fewer charge storage devices and/or smaller capacity charge storage device), while the scheduled nightly communications session will call for another type of charging operation (e.g., more charge storage devices and/or larger capacity charge storage device). The ED action associated with the standard alert may also call for a different signal strength and/or different data packet size as compared to a nightly communications session.

At 208-212, the process dispatches a charge instruction to charge the charge bank 19 from the battery 12 with supplemental energy. Among other things, the charge instruction may direct the constant current charger 16 and the charge bank 19 to initiate a corresponding type of charge (e.g., a trickle charge). The charge instruction may indicate the amount of supplemental energy to be added to the charge bank 19, a background period of time during which the charge bank 19 will be charged, and/or a background charge rate at which the constant current charger 16 delivers charged to the charge bank 19. Additionally or alternatively, when the charge bank 19 includes more than one charge storage device 21 (e.g., more than one capacitor), the charge instruction may direct the charge bank 19 to adjust the number of charge storage devices connected with one another to be charged. For example, the amount of supplemental energy may represent small, medium and large amounts. When a small amount of supplemental energy is desired, one or a small subset of the charge storage devices (e.g., capacitors) may be utilized from the charge bank 19, connected to the battery 12, and charged to a predetermined desired supplemental energy level. Alternatively, when a medium amount of supplemental energy is desired, a larger subset of the charge storage devices may be utilized from the charge bank 19. Additionally, when a large amount of supplemental energy is desired, all of the charge storage devices from the charge bank 19 may be utilized. For example, a BLE communications session that simply transmits an alert message, and little else, may utilize a small amount of supplemental energy, whereas a monitoring operation that collects impedance data and/or accelerometer activity signals may utilize a medium amount of supplemental energy, while a therapy operation that delivers pacing pulses may utilize a large amount of supplemental energy.

Additionally or alternatively, the charge operations at 208-212 may utilize a common charge storage device, but instead adjust the level to which the charge storage device is charged with supplemental energy (e.g., low, medium, high). The amount of supplemental energy may be controlled by setting a background charge time and background charge rate utilized by the constant current charger 16. Additionally or alternatively, the charge operations at 208-212 may utilize entirely separate charge storage devices, each of which is configured to have a different maximum capacity for supplemental energy, to provide a more efficient charge network. For example, the charge bank may have small, medium and large charge storage devices/capacitors. During the operation at 208, the small charge storage device may be connected and charged to a substantially full level, without utilizing the medium and large charge storage devices. During the operation at 210, the medium charge storage device may be connected and charged to a substantially full level, without utilizing the small and large charge storage devices. During the operation at 212, the large charge storage device may be connected and charged to a substantially full level, without utilizing the small and medium charge storage devices. The charging operations at 208-212 are performed prior to implementation of the ED action at a background charge rate. The background charge rate is lower than an energy demand rate at which the device operational circuitry and transceiver circuit consume energy during an ED action. As nonlimiting examples, the background charge rate may be less than 75%, and more preferably less than 60% or between 10-50% of the energy demand associated with the ED action to be performed by the device operational circuitry. By utilizing a background charge rate that is lower than the energy demand rate associated with the ED action, embodiments herein avoid the risk of causing an undesired battery voltage dip. Additionally or alternatively, the background charge rate may be fixed at a predetermined background charge rate, where the different charging operations at 208-212 vary over a period of time over which the charge bank 19 is charged. For example, when the charging operations 208-212 all utilize a common predetermined background charge rate, the operations at 208-212 may be performed for corresponding different periods of time (e.g., less than 2 seconds for a small amount of supplemental energy, 2-5 seconds for a medium amount of supplemental energy, more than five seconds for a large amount of supplemental energy).

Once the corresponding charge operation at 208-212 is completed, flow moves to 222. At 222, the process executes one or more ED actions. Next, flow moves to 214 where the process determines whether the scheduled ED action(s) have been completed. When the scheduled ED action(s) are completed, flow returns to 202 where the medical device returns to the low-power state. Alternatively, when the scheduled ED actions are not completed, flow returns to the dispatcher at 206.

Optionally, the dispatcher 206 may not always implement the charging operations at 208-212 in connection with a particular ED action. When the battery is in good condition (e.g., not near end of life and/or not exhibiting an ESR below a nominal battery charge threshold), the dispatcher 206 may skip the charging operations at 208-212 for various types of transmission operations, monitoring operations and therapy operations. For example, when the battery is not near end of life or exhibits a good battery power state (e.g., charged above a nominal battery charge threshold), the medical device need not charge the charge bank with supplemental energy. Instead, when the battery is early or in the middle of normal battery life and exhibits a strong battery charge level, in the event the ED action represents delivery of a pacing pulse, ATP therapy and the like, the dispatcher 206 may implement the therapy through a normal course of operation without initiating a charging operation for supplemental energy.

The operations at 216-220 may be implemented separately or in parallel with the above discussed operations. At 216, the process determines a supply state of the battery 12. For example, the process may perform a test periodically to test the state of the battery, such as to test the battery ESR and other battery state related parameters. The supply state of the battery may be defined in terms of a primary source limit. At 218, the process maintains an event history, such as to record an amount of energy that has been used by the medical device in the past. The event history may maintain cumulative energy usage information, as well as energy usage information associated with individual ED actions. At 220, the process analyzes past and future scheduled ED actions. For example, past scheduled ED actions may be analyzed to identify energy usage in connection there with. Based on the energy usage of the past scheduled ED actions, energy consumption estimates may be adjusted. The analysis at 220 of scheduled actions may also be utilized to reschedule events. For example, the dispatcher at 206 may determine that it is desirable to skip or delay an upcoming scheduled ED action, reorder multiple upcoming ED actions, or stagger operation of upcoming scheduled ED actions. For example, when it is desirable to complete a data transmission to a separate device, the process may delay other operations, such as an upcoming heart sound sensing operation and the like. As another example, a data transmission may be suspended when an ATP pacing therapy is necessary to be delivered.

Figure 3:
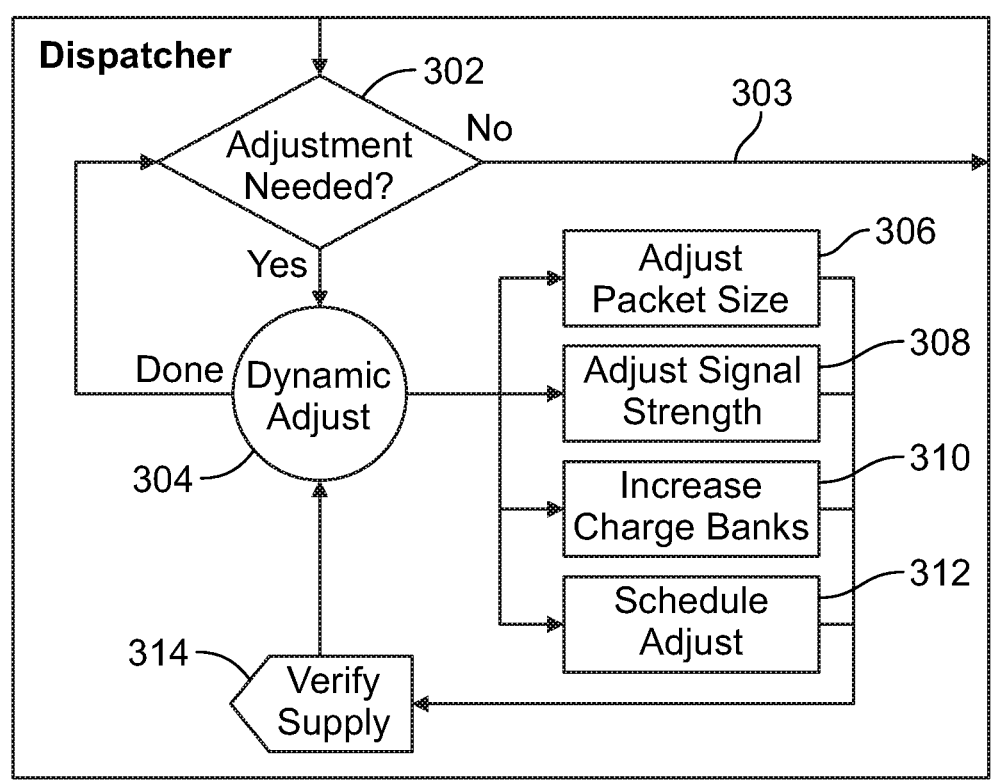
FIG. 3 illustrates a functional block diagram of the dispatcher in accordance with embodiments herein.

FIG. 3 illustrates a functional block diagram of the dispatcher 206 formed in accordance with embodiments herein. By way of example, the dispatcher 206 may be implemented, as part of the energy management module 14 (FIG. 1), in hardware, firmware or by a processor executing programmable instructions. The dispatcher 206 begins at 302 where parameters associated with the scheduled ED action are analyzed to determine whether an adjustment is needed in connection with one or more parameters associated with the scheduled ED action. When the dispatcher 206 determines that no adjustments in the parameters are needed, flow moves along 303 (corresponding to the path from the dispatcher 206 to the charging operations 208-212 in FIG. 2).

Alternatively, when the dispatcher 206 determines that it is desirable to adjust a parameter associated with a scheduled ED action, flow moves to 304. At 304, the dispatcher determines which of the one or more parameters should be dynamically adjusted. Based on the determination at 304, flow moves to one or more of 306-312. At 306, a packet length/size parameter is adjusted to change a length/size of data packets transmitted by the transceiver from the medical device. For example, a data packet length/size may be defined to include 80 bytes, 60 bytes, or more or less. For example, when the power state of the battery is relatively low, the dispatcher may determine to reduce the data packet size from 80 bytes to 60 bytes to 20 bytes, etc. Optionally, when the battery power state drops to a relatively low level, the communications operations may be limited to basic alerts and transmission may be suspended for other types of data (e.g., cardiac activity signals, arrhythmia episodes, pulmonary arterial pressure measurements/trends, BGA data). In general, the medical device will be able to sustain a relatively good data rate (e.g., 80 bytes or more per packet) over a majority of the device's life. However, near the end of life of the battery, it may then be necessary to reduce the data rate. As another nonlimiting example, the data packet size may be reduced or increased based on the type of communication session, such as a remote session or a clinical session, respectively. The data packet size may be reduced when the medical device is communicating with a local external device (e.g., a patient's smart phone), while the data packet size may be increased when the medical device is communicating with a physician's programmer or other device at a medical facility.

At 308, a signal strength parameter is adjusted to change a signal strength used by the transceiver in connection with at least one of transmitting or receiving during a communications session and/or in connection with transmitting advertising packets. For example, signal strength may be reduced when prior communications have exhibited high signal quality (e.g., relatively low data packet losses and/or a relatively strong signal-to-noise ratio). Alternatively, when the signal quality is determined to drop, the signal strength may be increased in connection with the next scheduled communications session.

Optionally, the signal strength parameter, as well as any other aspect of the communications operations, may be managed dynamically in accordance with the methods, systems and devices described in US Published Patent Application 20190191468, published Jun. 20, 2019, titled "Managing Dynamic Connection Intervals For Implantable And External Devices", which is expressly incorporated herein by reference in its entirety.

At 310, the dispatcher changes a size of an "active" charge bank, such as by increasing or decreasing a number of charge storage devices or capacitors actively utilized. For example, as explained herein, the charge bank may include a series of capacitors or other charge storage devices, only a portion of which may be connected for use during any one charge operation. At 310, the number of charge storage devices that are active is adjusted by connecting additional or disconnecting charge storage devices. Additionally or alternatively, at 310, the dispatcher may determine the background charge rate to be utilized when charging the charge bank and/or a background period of time to set aside to allow the charge bank to charge before initiating the ED action.

At 312, the dispatcher changes one or more scheduling parameters associated with a packet transmission rate at which data packets are transmitted from the medical device. For example, the scheduling parameter may be adjusted to delay a transmission operation by changing the data transmission rate for transmitting data packets every one second to transmitting data packets every five seconds, or otherwise (also referred to as the cycle time). The cycle time or delay may be a predetermined period of time or clock cycles, or alternatively dynamically determined based on the nature of the ED action and/or the battery state. For example, the dispatcher may determine that the battery is in a weak state and thus the cycle time or delay between data packets may be extended by a predetermined period of time. Accordingly, the dispatcher may adjust the schedule for the packet transmission rate, as compared to a faster packet transmission rate that may be utilized when the battery is in a stronger state.

The foregoing discussion of the parameter adjustments at 306-312 may be implemented individually or in various parallel combinations. For example, it may be desirable to increase the signal strength, but decrease the packet transmission rate. As a further example it may be desirable to increase the data packet size, while decreasing the rate at which data packets are transmitted. As a further example, it may be desirable to increase the number of active charge storage devices in the charge bank, while also adjusting signal strength and/or data packet size.

It is recognized that the parameters discussed in connection with the operations at 306-312 are merely examples of the types of parameters that may be adjusted. Other types of parameters related to a communications operation may be adjusted in addition to or in place of the operations at 306, 308 and 312. Further, it is recognized that embodiments herein may adjust other types of parameters that are not related to a communications operation, but instead relate to in operation for monitoring a COI and/or determining/delivering a therapy. Following the operations at 306-312, flow moves to 314.

At 314, the dispatcher implements a verify supply operation to identify a battery power state. For example, the battery power state may be indicated by analyzing a supply voltage rail for the battery to determine whether the potential exists that the battery voltage will drop below a predetermined battery voltage lower threshold. The verify supply operation identifies a battery power state as an input into a feedback loop iteratively performed by the dispatcher to determine whether a further dynamic adjustment at 304 is warranted. As a nonlimiting example, the supply voltage rail may be measured to be 2.6 V and the lower threshold may be 2.5 V, where a battery voltage drop below 2.5 V may result in an undesired action by the medical device (e.g., a reset operation). The verify supply operation ensures that the battery does not drop unduly low, thereby allowing for a dynamic management operation that adjusts for different types and conditions of batteries (e.g., as indicated by different ESR levels).

FIG. 4 provides a sectional view of a patient's heart 33 and shows a leadless intra-cardiac medical device 400. The leadless implantable medical device 400 has been placed through the superior vena cava 28 into the right atrium 30 of the heart 33. FIG. 4 also shows the inferior vena cava 35, the left atrium 36, the right ventricle 37, the left ventricle 40, the atrial septum 41 that divides the two atria 30, 36, the ventricular vestibule W, the right atrial appendage (RAA), and the tricuspid valve 42 between the right atrium 30 and right ventricle 37. The reader will appreciate that the view of FIG. 4 is simplified and somewhat schematic, but that nevertheless FIG. 4 and the other views included herein will suffice to illustrate adequately the placement and operation of embodiments of the present invention. The term "septum" shall be used throughout to generally refer to any portion of the heart separating two chambers (e.g., RA to LA, RV to LV). The leadless implantable medical device (LIMD) 400 is formed in accordance with an embodiment. The LIMD 400 may represent a pacemaker that functions in a DDD mode or a DDDR-mode, a cardiac resynchronization device, a cardioverter, a defibrillator and the like. When in DDD or DDDR-mode, the LIMD 400 may sense in two chambers, pace in two chambers and inhibit pacing in either chamber based on intrinsic events sensed in that chamber or in the other chamber. The LIMD 400 comprises a housing configured to be implanted entirely within a single local chamber of the heart. For example, the LIMD 400 may be implanted entirely and solely within the right atrium or entirely and solely within the right ventricle. Optionally, the LIMD 400 may be implanted entirely and solely within the left atrium or left ventricle through more invasive implant methods.

For convenience, hereafter the chamber in which the LIMD 400 is implanted shall be referred to as the "local" chamber. The local chamber includes a local chamber wall that is physiologically response to local activation events originating in the local chamber. The local chamber is at least partially surrounded by local wall tissue that forms or constitutes at least part of a conduction network for the associated chamber. For example, during normal operation, the wall tissue of the right atrium contracts in response to an intrinsic local activation event that originates at the sinoatrial (SA) node and in response to conduction that propagates along the atrial wall tissue. For example, tissue of the right atrium chamber wall in a healthy heart follows a conduction pattern, through depolarization, that originates at the SA node and moves downward about the right atrium until reaching the atria ventricular (AV) node. The conduction pattern moves along the chamber wall as the right atrium wall contracts.

The term "adjacent" chamber shall refer to any chamber separated from the local chamber by tissue (e.g., the RV, LV and LA are adjacent chambers to the RA; the RA and LV are adjacent chambers to the LA; the RA and RV are adjacent to one another; the RV and LV are adjacent to one another, and the LV and LA are adjacent to one another).

The local chamber (e.g., the right atrium) has various tissue of interest, such as a septum, that separate the local chamber from the adjacent chambers (e.g., right ventricle, left atrium, left ventricle). In certain portions or segments of the septum, segments of the septum, behave in physiologically different manners. For example, in certain segments of the septum for the right atrium, even during normal healthy operation, the septum wall tissue does not propagate the conduction in the same manner or pattern as in a majority of the wall tissue of the right atrium wall. For example, septum wall tissue in the right atrium, referred to as the ventricular vestibule tissue, does not behave physiologically in the same manner as the non-septum atrial wall tissue. Instead, the right ventricular vestibule tissue is physiologically coupled to the wall tissue in the right ventricle and in accordance therewith exhibits a conduction pattern that follows the conduction pattern of the right ventricular wall tissue. The right ventricular vestibule tissue is one example of a septum segment that partially separates a local chamber (e.g., the right atrium) from an adjacent chamber (e.g., right ventricle), yet is physiologically coupled to conduction in the adjacent chamber (e.g., right ventricle).

FIGS. 5A and 5B illustrate the LIMD 400 in more detail. FIG. 5A illustrates a side perspective view of the LIMD 400 of FIG. 4 oriented with the base 504 facing upward to illustrate electrodes 510-512 in more detail. FIG. 5B illustrates a bottom plan view of the LIMD 400. The LIMD 400 comprises a housing 502 having a proximal base 504, a distal top end 506, and an intermediate shell 508 extending between the proximal base 504 and the distal top end 506. The shell 508 is elongated and tubular in shape and extends along a longitudinal axis 509.

The base 504 includes one or more electrodes 510-512 securely affixed thereto and projected outward. For example, the outer electrodes 510, 511 may be formed as large semi-circular spikes or large gauge wires that wrap only partially about the inner electrode 512. The electrodes 510, 511 may be located on opposite sides of, and wound in a common direction with, the inner electrode 512. The first or outer electrodes 510, 511 are provided directly on the housing 502 of the LIMD 400 at a first position, namely at or proximate a periphery of the base 504 of the housing. The outer electrodes 510, 511 are positioned near the periphery of the base 504 such that, when the LIMD 400 is implanted in the local chamber (e.g., right atrium), the outer electrodes 510, 511 engage the local chamber wall tissue at tissue of interest for a local activation site that is near the surface of the wall tissue, and that is within the conduction network of the local chamber. The outer electrodes 510, 511 are physically separated or bifurcated from one another and have separate distal outer tips 515, 516. The outer electrodes 510, 511 are electrically joined to one another (i.e., common), but are electrically separated from the inner electrode 512. The second or inner electrode 512 is also provided directly on the housing 502 of the LIMD 400 at a second position, namely at or proximate to a central portion of the base 504 of the housing.

The LIMD 400 includes a controller 520, a transceiver circuit 522, MIT operational circuitry 524, a battery 526 and a charge bank 527. It is recognized that the LIMD 400 includes additional circuitry and other components. The controller 520 implements the operations described herein in connection with managing energy usage. Among other things, the controller 520 may implement the energy management module 14 of FIG. 1. The dispatcher (described in connection with FIGS. 2 and 3) may be implemented by the controller 520 and/or other firmware or hardware. Among other things, the controller 520 is configured to identify an ED action to be performed by device operational circuitry in connection with at least one of monitoring a medical COI, treating the medical COI, or wirelessly communicating with a separate device. While illustrated as separate blocks, it is recognized that the controller 520 and transceiver circuit 522 represent a portion of the device operational circuitry. The controller 520 obtains an energy consumption estimate for an amount of energy to be consumed by the device operational circuitry (including the controller 520 and transceiver circuit 522) in connection with performing the ED action. The controller 520 dispatches, based on the energy consumption estimate, a charge instruction to charge the charge bank 527 from the battery 526 with supplemental energy. The controller 520 supplies the supplemental energy, from the charge bank 527, to the device operational circuitry for performing the ED action in connection with the at least one of monitoring, treating or communicating operations.

The electrodes 510-512 may be used to deliver lower energy or high energy stimulus, such as pacing pulses, cardioverter pulse trains, defibrillation shocks and the like. The electrodes 510-512 may also be used to sense electrical activity, such as physiologic and pathologic behavior and events and provide sensed signals to the transceiver circuit 522. The electrodes 510-512 are configured to be joined to an energy source, such as a charge storage unit. The electrodes 510-512 receive stimulus pulse(s) from the charge storage unit. The electrodes 510-512 may be the same or different size. The electrodes 510-512 are configured to deliver high or low energy stimulus pulses to the myocardium.

The controller 520 manages delivery of pacing pulses through the electrodes 510-512 in a synchronous manner. The stimulus pulses are delivered synchronously to local and distal activation sites in the local and distal conduction networks such that stimulus pulses delivered at the distal activation site are timed to cause contraction of the adjacent chamber in a predetermined relation to contraction of the local chamber. The inner and outer electrodes 510-512 are spaced radially and longitudinally apart from one another such that the local activation site (e.g., right atrium) and the distal activation side in the adjacent chamber (e.g., right ventricle) are sufficiently remote from one another within the heart's conductive network to initiate activation in different branches of the hearts conductive network in a time relation that corresponds to the normal hemodynamic timers (e.g., AV delay).

The controller 520 may operate the LIMD 400 in various modes, such as in select pacemaker modes, select cardiac resynchronization therapy modes, a cardioversion mode, a defibrillation mode and the like. For example, a typical pacing mode may include DDIR, R, DDOR and the like, where the first letter indicates the chamber(s) paced (e.g., A: Atrial pacing; V: Ventricular pacing; and D: Dual-chamber (atrial and ventricular) pacing). The second letter indicates the chamber in which electrical activity is sensed (e.g., A, V, or D). The code 0 is used when pacemaker discharge is not dependent on sensing electrical activity. The third letter refers to the response to a sensed electric signal (e.g., T: Triggering of pacing function; I: Inhibition of pacing function; D: Dual response (i.e., any spontaneous atrial and ventricular activity will inhibit atrial and ventricular pacing and lone atrial activity will trigger a paced ventricular response) and O: No response to an underlying electric signal (usually related to the absence of associated sensing function)). The fourth letter indicates rate responsive if R is present.

FIG. 6 shows an exemplary LIMD 600 configured for dual-chamber functionality from a primary location within a single chamber of the heart. For example, the LIMD 600 may be implemented as a pacemaker, equipped with both atrial and ventricular sensing and pacing circuitry. Alternatively, the LIMD 600 may be implemented with a reduced set of functions and components. For instance, the LIMD 600 may be implemented without ventricular sensing and pacing. The LIMD 600 may also be implemented with an increased set of functions. For example, if the LIMD 600 includes a coil type electrode, the LIMD may be configured to include cardioversion and/or shocking therapy capability.

The LIMD 600 has a housing 601 to hold the electronic/computing components. The housing 601 (which is often referred to as the "can", "case", "encasing", or "case electrode") may be programmably selected to act as the return electrode for certain stimulus modes. Housing 601 further includes a plurality of terminals 602, 604, 606, 608, 610 that interface with electrodes of the LIMD. For example, the terminals may include: a terminal 602 that connects with a first electrode associated with the housing (e.g., electrode) and located in a first chamber; a terminal 604 that connects with a second electrode associated with the housing (e.g., electrode) and also located in the first chamber; a terminal 606 that connects with a third electrode associated with the housing (e.g., electrode) and located in the first chamber and possibly partially extending into tissue associated with a second chamber; and two additional terminals 608, 610 that connect with one or more additional electrodes (e.g., electrode), if available. The type and location of each electrode may vary. For example, the electrodes may include various combinations of ring, tip, coil and shocking electrodes and the like.

The LIMD 600 includes a programmable microcontroller 620 that controls various operations of the LIMD 600, including cardiac monitoring and stimulation therapy. Microcontroller 620 includes a microprocessor (or equivalent control circuitry), RAM and/or ROM memory, logic and timing circuitry, state machine circuitry, and I/O circuitry.

The LIMD 600 further includes a first chamber pulse generator 622 that generates stimulation pulses for delivery by one or more electrodes coupled thereto. The pulse generator 622 is controlled by the microcontroller 620 via control signal 624. The pulse generator 622 is coupled to the select electrode(s) via an electrode configuration switch 626, which includes multiple switches for connecting the desired electrodes to the appropriate I/O circuits, thereby facilitating electrode programmability. The switch 626 is controlled by a control signal 628 from the microcontroller 620.

In the example of FIG. 6, a single pulse generator 622 is illustrated. Optionally, the LIMD 600 may include multiple pulse generators, similar to pulse generator 622, where each pulse generator is coupled to one or more electrodes and controlled by the microcontroller 620 to deliver select stimulus pulse(s) to the corresponding one or more electrodes.

Microcontroller 620 is illustrated as including timing control circuitry 632 to control the timing of the stimulation pulses (e.g., pacing rate, atrio-ventricular (AV) delay etc.). The timing control circuitry 632 may also be used for the timing of refractory periods, blanking intervals, noise detection windows, evoked response windows, alert intervals, marker channel timing, and so on. Microcontroller 620 also has an arrhythmia detector 634 for detecting arrhythmia conditions. Although not shown, the microcontroller 620 may further include other dedicated circuitry and/or firmware/software components that assist in monitoring various conditions of the patient's heart and managing pacing therapies.

The LIMD 600 includes sensing circuitry 644 selectively coupled to one or more electrodes through the switch 626. The sensing circuitry detects the presence of cardiac activity in the right chambers of the heart. The sensing circuitry 644 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit 602 to sense low amplitude signal characteristics of atrial fibrillation. Switch 626 determines the sensing polarity of the cardiac signal by selectively closing the appropriate switches. In this way, the clinician may program the sensing polarity independent of the stimulation polarity.

The output of the sensing circuitry 644 is connected to the microcontroller 620 which, in turn, triggers or inhibits the pulse generator 622 in response to the absence or presence of cardiac activity. The sensing circuitry 644 receives a control signal 646 from the microcontroller 620 for purposes of controlling the gain, threshold, polarization charge removal circuitry (not shown), and the timing of any blocking circuitry (not shown) coupled to the inputs of the sensing circuitry.

In the example of FIG. 6, a single sensing circuit 644 is illustrated. Optionally, the LIMD 600 may include multiple sensing circuit, similar to sensing circuit 644, where each sensing circuit is coupled to one or more electrodes and controlled by the microcontroller 620 to sense electrical activity detected at the corresponding one or more electrodes. The sensing circuit 644 may operate in a unipolar sensing configuration or in a bipolar sensing configuration.

The LIMD 600 further includes an analog-to-digital (ND) data acquisition system (DAS) 650 coupled to one or more electrodes via the switch 626 to sample cardiac signals across any pair of desired electrodes. The data acquisition system 650 is configured to acquire intracardiac electrogram signals, convert the raw analog data into digital data, and store the digital data for later processing and/or telemetric transmission to an external device 654 (e.g., a programmer, local transceiver, or a diagnostic system analyzer). The data acquisition system 650 is controlled by a control signal 656 from the microcontroller 620.

The microcontroller 620 is coupled to a memory 660 by a suitable data/address bus 662. The programmable operating parameters used by the microcontroller 620 are stored in memory 660 and used to customize the operation of the LIMD 600 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy. The operating parameters of the LIMD 600 may be non-invasively programmed into the memory 660 through a telemetry circuit 664 in telemetric communication via communication link 666 with the external device 654. The telemetry circuit 664 allows intracardiac electrograms and status information relating to the operation of the LIMD 600 (as contained in the microcontroller 620 or memory 660) to be sent to the external device 654 through the established communication link 666.

The microcontroller 620 includes an energy management module 636 that implements the operations described herein. Among other things, the energy management module 636 implements the process of FIG. 2 and the dispatcher of FIG. 3. The energy management module 636 implements the operations described herein in connection with managing energy usage. The dispatcher (described in connection with FIGS. 2 and 3) may be implemented by the energy management module 636 and/or other firmware or hardware. Among other things, the energy management module 636 is configured to identify an ED action to be performed by device operational circuitry in connection with at least one of monitoring a medical COI, treating the medical COI, or wirelessly communicating with a separate device. While illustrated as separate blocks, it is recognized that the energy management module 636 and telemetry circuit 564 represent a portion of the device operational circuitry. The energy management module 636 obtains an energy consumption estimate for an amount of energy to be consumed by the device operational circuitry (including the controller 620 and telemetry circuit 664) in connection with performing the ED action. The energy management module 636 dispatches, based on the energy consumption estimate, a charge instruction to charge the charge bank 639 from the battery 672 with supplemental energy. The energy management module 636 supplies the supplemental energy, from the charge bank 639, to the device operational circuitry for performing the ED action in connection with the at least one of monitoring, treating or communicating operations.

During a supplemental charging operation, the switch 637 connects the battery 672 to the charge bank 639. The constant current charger 638 manages the charging operation to charge the charge bank 639 at a background charging rate for a background charge time period.

The LIMD 600 can further include magnet detection circuitry (not shown), coupled to the microcontroller 620, to detect when a magnet is placed over the unit. A magnet may be used by a clinician to perform various test functions of the unit 602 and/or to signal the microcontroller 620 that the external programmer 654 is in place to receive or transmit data to the microcontroller 620 through the telemetry circuits 664.

The LIMD 600 may be equipped with a communication modem (modulator/demodulator) 640 to enable wireless communication with a remote device, such as a second implanted LIMD in a master/slave arrangement, such as described in U.S. Pat. No. 7,630,767. In one implementation, the communication modem 640 uses high frequency modulation. As one example, the modem 640 transmits signals between a pair of LIMD electrodes, such as between the LIMD 600 and anyone of the electrodes connected to terminals 602-610. The signals are transmitted in a high frequency range of approximately 20-80 kHz, as such signals travel through the body tissue in fluids without stimulating the heart or being felt by the patient. The communication modem 640 may be implemented in hardware as part of the microcontroller 620, or as software/firmware instructions programmed into and executed by the microcontroller 620. Alternatively, the modem 640 may reside separately from the microcontroller as a standalone component.

The LIMD 600 can further include one or more physiologic sensors 670. Such sensors are commonly referred to as "rate-responsive" sensors because they are typically used to adjust pacing stimulation rates according to the exercise state of the patient. However, the physiological sensor 670 may further be used to detect changes in cardiac output, changes in the physiological condition of the heart, or diurnal changes in activity (e.g., detecting sleep and wake states). Signals generated by the physiological sensors 670 are passed to the microcontroller 620 for analysis. The microcontroller 620 responds by adjusting the various pacing parameters (such as rate, AV Delay, V-V Delay, etc.) at which the atrial and ventricular pacing pulses are administered. While shown as being included within the unit 602, the physiologic sensor(s) 670 may be external to the unit 602, yet still be implanted within or carried by the patient. Examples of physiologic sensors might include sensors that, for example, sense respiration rate, pH of blood, ventricular gradient, activity, position/posture, temperature, minute ventilation (MV), and so forth.

A battery 672 provides operating power to all of the components in the LIMD 600. The battery 672 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 672 also desirably has a predictable discharge characteristic so that elective replacement time can be detected. As one example, the unit 602 employs lithium/silver vanadium oxide batteries.

The LIMD 600 further includes an impedance measuring circuit 674, which can be used for many things, including: impedance surveillance during the acute and chronic phases for proper LIMD positioning or dislodgement; detecting operable electrodes and automatically switching to an operable pair if dislodgement occurs; measuring respiration or minute ventilation; measuring thoracic impedance; detecting when the device has been implanted; measuring stroke volume; and detecting the opening of heart valves; and so forth. The impedance measuring circuit 674 is coupled to the switch 626 so that any desired electrode may be used.

The microcontroller 620 further controls a shocking circuit 680 by way of a control signal 682. The shocking circuit 680 generates shocking pulses of low (e.g., up to 0.5 joules), moderate (e.g., 0.5-10 joules), or high energy (e.g., 611 to 40 joules), as controlled by the microcontroller 620. Such shocking pulses are applied to the patient's heart through shocking electrodes, if available on the LIMD. It is noted that the shock therapy circuitry is optional and may not be implemented in the LIMD, as the various LIMDs described above and further below will typically not be configured to deliver high voltage shock pulses. On the other hand, it should be recognized that an LIMD may be used within a system that includes backup shock capabilities, and hence such shock therapy circuitry may be included in the LIMD.

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

All references, including publications, patent applications and patents, cited herein are hereby incorporated by reference to the same extent as if each reference were individually and specifically indicated to be incorporated by reference and were set forth in its entirety herein.

What is claimed is:

1. A medical device, comprising:
a battery;
a charge bank configured to store supplemental energy;
memory to store program instructions; and
device operational circuitry that includes at least one of a transceiver, circuitry or processor configured to execute the program instructions, the device operational circuitry configured to:
identify an energy demand (ED) action to be performed by the device operational circuitry in connection with at least one of monitoring a medical characteristic of interest (COI), treating the medical COI, or wirelessly communicating with a separate device;
obtain an energy consumption estimate for an amount of energy to be consumed by the device operational circuitry in connection with performing the ED action;
dispatch, based on the energy consumption estimate, a charge instruction to charge the charge bank from the battery with supplemental energy;
connect the charge bank to form a power supply loop formed between the battery and at least one of the transceiver, circuitry or processor, to supply the supplemental energy, from the charge bank in addition to primary energy from the battery, to the device operational circuitry for performing the ED action in connection with the at least one of monitoring, treating or communicating operations; and switch the charge bank in and out of the power supply loop based on the energy consumption estimate.

2. The device of claim 1, wherein the device operational circuitry is further configured to perform the switch based on when the energy consumption estimate exceeds an energy threshold.

3. The device of claim 1, wherein the device operational circuitry is configured to add the supplemental power from the charge bank when the battery cannot supply the energy consumption estimate without experiencing a battery voltage dip below a battery voltage threshold.

4. The device of claim 1, wherein the charge instruction is configured to perform a background charging operation to selectively interconnect the charge bank to the battery prior to a scheduled time before the ED action, the background charging operation to siphon energy from the battery at a predetermined background charge rate that avoids the battery from experiencing a battery voltage dip below a battery voltage threshold.

5. The device of claim 1, wherein the battery exhibits a primary source limit, the charge bank supplying the supplemental power when the energy consumption estimate exceeds the primary source limit.

6. The device of claim 1, wherein the device operational circuitry is further configured to implement first or second charge operations to the charge bank based on a type of the ED action.

7. The device of claim 6, wherein the charge bank comprises multiple capacitors, from which a subset of the multiple capacitors is activated based on an amount of the supplemental energy associated with the type of the ED action.

8. The device of claim 1, wherein the energy consumption estimate estimates the power demand associated with performing a communicating operation contemporaneous in time with at least one of the monitoring or treating operations, the device operational circuitry further comprising a dispatcher configured to at least one of skip, delay or modify the at least one of monitoring or treating operation when the energy consumption estimate exceeds a primary source limit of the battery.

9. The device of claim 1, wherein the medical device represents at least one of an implantable medical device, a diabetes monitoring device, a body generated analyte (BGA) test device, and a pulmonary arterial pressure monitor.

10. A medical device, comprising:
a battery;
a charge bank configured to store supplemental energy;
memory to store program instructions; and
device operational circuitry that includes at least one of a transceiver, circuitry or processor configured to execute the program instructions, the device operational circuitry configured to:
identify an energy demand (ED) action to be performed by the device operational circuitry in connection with at least one of monitoring a medical characteristic of interest (COI), treating the medical COI, or wirelessly communicating with a separate device;
obtain an energy consumption estimate for an amount of energy to be consumed by the device operational circuitry in connection with performing the ED action;
dispatch, based on the energy consumption estimate, a charge instruction to charge the charge bank from the battery with supplemental energy;
connect the charge bank to the battery to supply the supplemental energy, from the charge bank in addition to primary energy from the battery, to the device operational circuitry for performing the ED action in connection with the at least one of monitoring, treating or communicating operations,
wherein the ED action includes initiating a wireless communications session, the device operational circuitry includes a dispatcher configured to dynamically adjust a transmission parameter utilized in connection with the wireless communications session, the transmission parameter that is updated including adjusting at least one of transmit packet size, transmit packet number, packet transmission rate, or signal power.

11. A method for managing energy usage of a medical device, the method comprising:
identifying an energy demand (ED) action to be performed by device operational circuitry of the medical device in connection with at least one of monitoring a medical characteristic of interest (COI), treating the medical COI, or wirelessly communicating with a separate device, the device operational circuitry including at least one of a transceiver, circuitry or processor;
obtaining an energy consumption estimate for an amount of energy to be consumed by the device operational circuitry in connection with performing the ED action;
dispatching, based on the energy consumption estimate, a charge instruction to charge a charge bank from a battery with supplemental energy;
connecting the charge bank to form a power supply loop formed between the battery and at least one of the transceiver, circuitry or processor, for supplying the supplemental energy, from the charge bank in addition to primary energy from the battery, to the device operational circuitry for performing the ED action in connection with the at least one of monitoring, treating or communicating operations; and
switching the charge bank in and out of the power supply loop based on the energy consumption estimate.

12. The method of claim 11, wherein the switching is based on when the energy consumption estimate exceeds an energy threshold.

13. The method of claim 11, wherein the supplying operation adds the supplemental power from the charge bank when the battery cannot supply the energy consumption estimate without experiencing a battery voltage dip below a battery voltage threshold.

14. The method of claim 11, further comprising performing a background charging operation to selectively interconnect the charge bank to the battery prior to a scheduled time before the ED action, the background charging operation siphoning energy from the battery at a predetermined background charge rate that avoids the battery from experiencing a battery voltage dip below a battery voltage threshold.

15. The method of claim 11, wherein the ED action includes initiating a wireless communications session, the method further comprising dynamically adjusting a transmission parameter utilized in connection with the wireless communications session, the transmission parameter that is updated including adjusting at least one of transmit packet size, transmit packet number, packet transmission rate, or signal power.

16. The method of claim 11, wherein the battery exhibits a primary source limit, the charge bank supplying the supplemental power when the energy consumption estimate exceeds the primary source limit.

17. The method of claim 11, further comprising implementing one of first or second charge operations of the charge bank based on a type of the ED action, the first and second charge operations having different first and second supplemental energies, respectively.

18. The method of claim 11, wherein the charge bank comprises multiple capacitors, the method further comprising activating a subset of the multiple capacitors based on an amount of the supplemental energy associated with a type of the ED action.

19. The method of claim 11, further comprising verifying a battery state and dynamically adjusting a parameter in connection with at least one of the monitoring, treating or communicating operations based on the battery state.

20. A method for managing energy usage of a medical device, the method comprising:

identifying an energy demand (ED) action to be performed by device operational circuitry of the medical device in connection with at least one of monitoring a medical characteristic of interest (COI), treating the medical COI, or wirelessly communicating with a separate device, the device operational circuitry including at least one of a transceiver, circuitry or processor;

obtaining an energy consumption estimate for an amount of energy to be consumed by the device operational circuitry in connection with performing the ED action;

dispatching, based on the energy consumption estimate, a charge instruction to charge a charge bank from a battery with supplemental energy; and connecting the charge bank to the battery for supplying the supplemental energy, from the charge bank in addition to primary energy from the battery, to the device operational circuitry for performing the ED action in connection with the at least one of monitoring, treating or communicating operations, wherein the obtaining the energy consumption estimate estimates the power demand associated with performing a communicating operation contemporaneous in time with at least one of the monitoring or treating operations, the method further comprising at least one of skipping, delaying or modifying the at least one of monitoring or treating operation when the energy consumption estimate exceeds a primary source limit of the battery.

* * * * *